United States Patent
Picard et al.

[11] Patent Number: 5,123,037
[45] Date of Patent: Jun. 16, 1992

[54] METHOD FOR CALIBRATING THE MEASURING SYSTEM OF AN X-RAY APPARATUS

[75] Inventors: Catherine Picard, Boulogne; Anne Rougee, Fontenay aux Roses; Didier Saint-Felix, Boulogne; Yves Trousset, Paris, all of France

[73] Assignee: General Electric CGR S.A., Issy Les Moulineaux, France

[21] Appl. No.: 627,766

[22] Filed: Dec. 14, 1990

[30] Foreign Application Priority Data

Dec. 14, 1989 [FR] France .................. 89 16568

[51] Int. Cl.⁵ .............................................. H05G 1/64
[52] U.S. Cl. .................................... 378/99; 378/62; 378/207; 358/111
[58] Field of Search ............. 378/18, 54, 56, 62, 378/99, 207; 358/111

[56] References Cited

U.S. PATENT DOCUMENTS

| | | |
|---|---|---|
| 4,068,306 | 1/1978 | Chen et al. |
| 4,571,491 | 2/1982 | Vinegar et al. ............ 378/207 |
| 4,686,695 | 8/1987 | Macovski. |
| 4,980,904 | 12/1990 | Sones et al. ............ 378/207 |

FOREIGN PATENT DOCUMENTS 0321289  6/1989  European Pat. Off.

OTHER PUBLICATIONS

Med. Phys. 13 (3), May/Jun. 1986, pp. 334-339, W. A. Kalender, et al., "Evaluation of a Prototype Dual-Energy Computed Tomographic Apparatus, 1. Phantom Studies $^a$)".

Primary Examiner—Janice A. Howell
Assistant Examiner—David P. Porta
Attorney, Agent, or Firm—Oblon, Spivak, McClelland, Maier & Neustadt

[57] ABSTRACT

In order to represent the bone structure of a patient's body, acquisitions are made with different irradiation energies. The irradiations are compared with these two energies in order to deduce a two-dimensional projected image which is representative of the bone structure alone. To this end, there is assigned to each pixel in the projected images a value corresponding to the thickness of bone traversed by an x-ray which has terminated at said pixel. This value is obtained by calibrating the measuring system, detector cell by detector cell, so as to correct the spatial non-uniformities of the acquisition system.

4 Claims, 3 Drawing Sheets

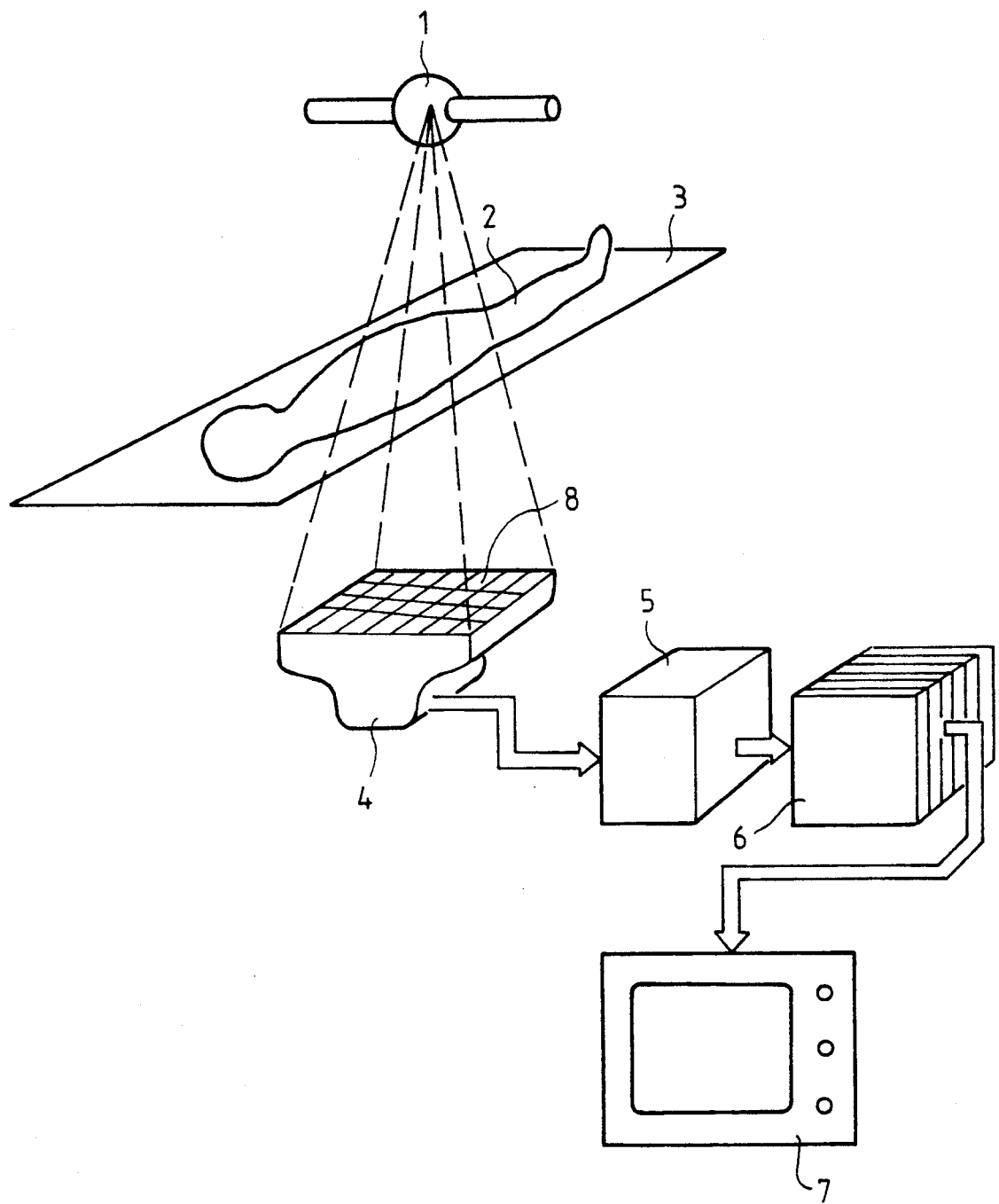
FIG_1

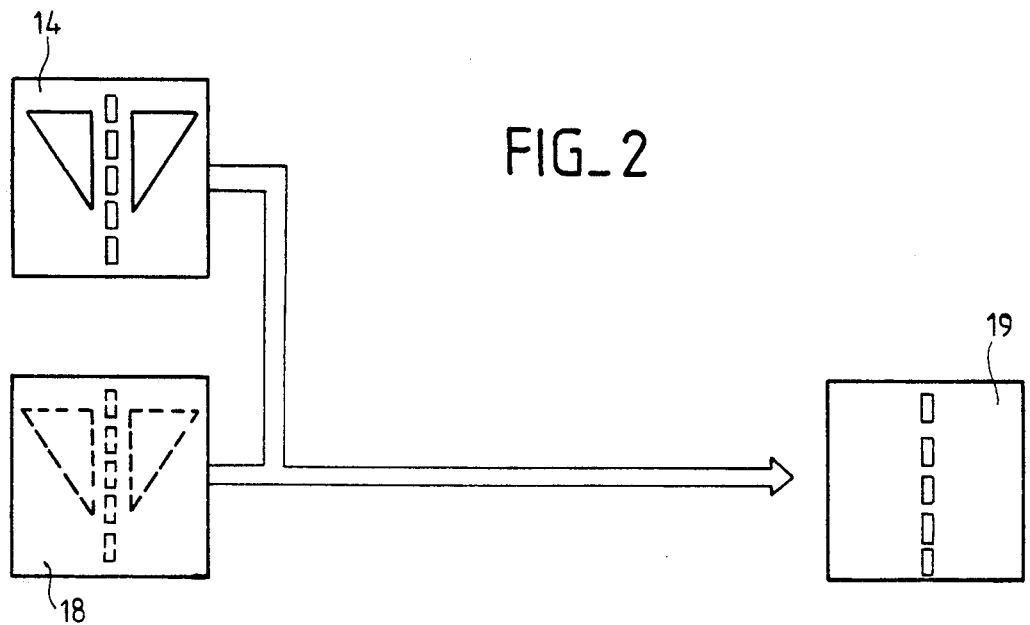
FIG_2
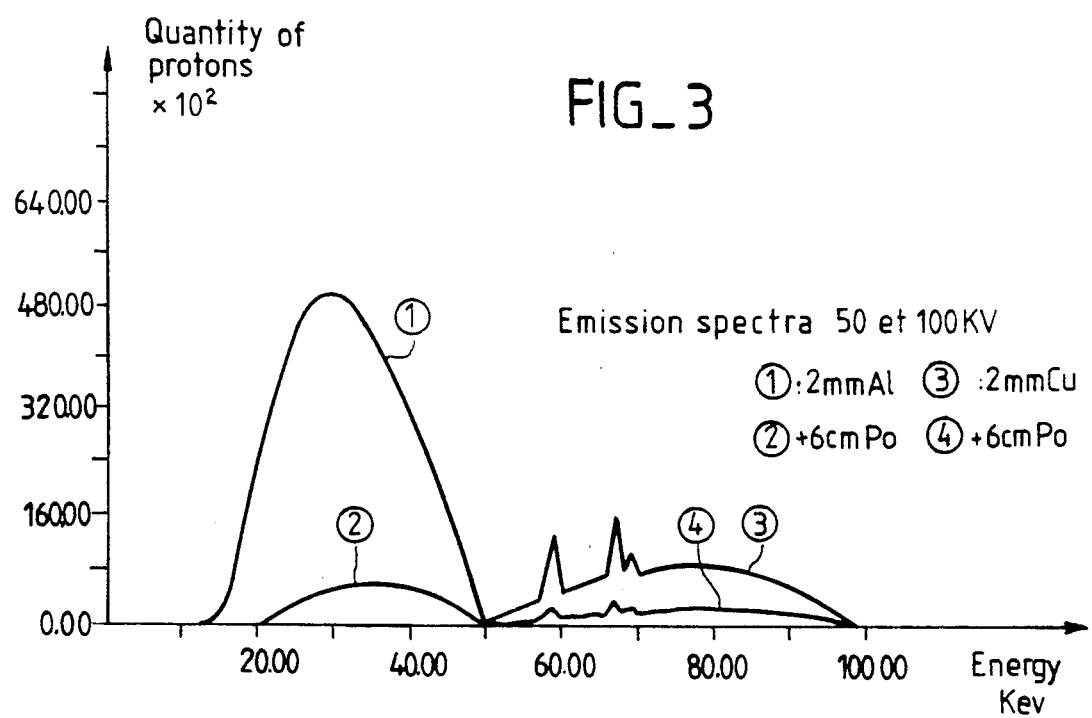
FIG_3
Emission spectra 50 et 100 KV
① : 2mm Al    ③ : 2mm Cu
② + 6cm Po   ④ + 6cm Po

FIG_4
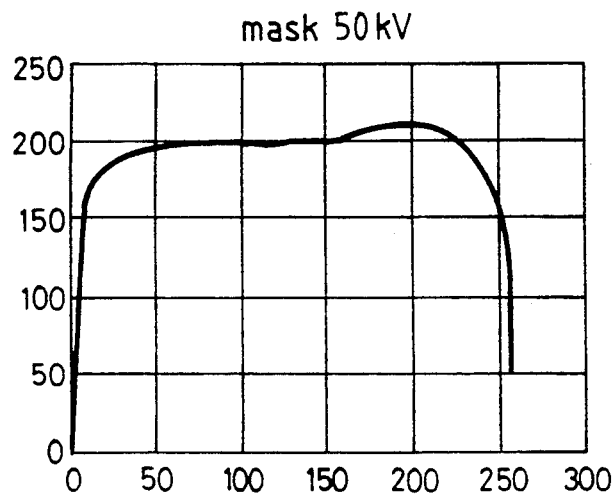
FIG_5
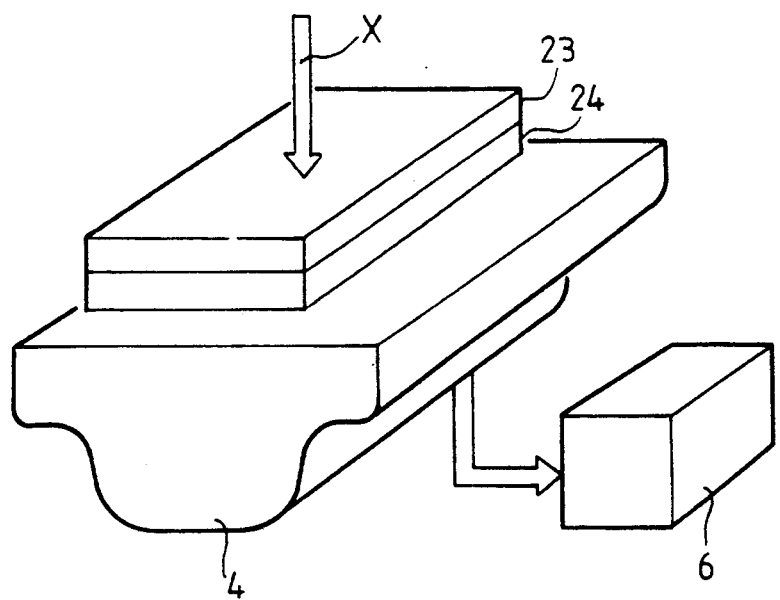

METHOD FOR CALIBRATING THE MEASURING SYSTEM OF AN X-RAY APPARATUS

BACKGROUND OF THE INVENTION

1. Field of the Invention

The present invention relates to a method for calibrating the measuring chain of an x-ray apparatus. The invention is more particularly applicable to the medical field in which the devices to be calibrated are mainly x-ray machines for carrying out dual-energy experiments. Potential applications can nevertheless be found in other fields.

2. Description of the Prior Art

In a pair of medical dual-energy experiments, a patient's body to be examined is subjected to a first irradiation during a first acquisition whilst the x-ray tube emits x-rays, the energy of which belongs to a first range. A first image is then acquired. The experiment is repeated for the second range and a second image is acquired. Starting from the two acquired images, other images are produced in which the value of the image elements is a function of an energy composition of the results of measurement of x-ray absorption contained in the two acquired images. The mode of energy composition of the images makes it possible in a typically medical application to extract in particular a two-dimensional image which is representative of the bone structures of a patient's body from the acquired images.

The basic principles of energy combination are known as "decomposition by dual energy". In the case of an object composed of two different materials (for example bone and soft tissues in the case considered here), this decomposition makes it possible to compute from two projected images of said object which are acquired with x-rays of different energies a projected image corresponding to the contribution of only one of the materials which constitute the object, namely bones in this instance.

These basic principles may be found in the following references: "A method for selective tissue and bone visualization using dual energy scanned projection radiography", W. R. Brody, G. Butt, A. Hall and A. Macovski, MED. PHYS., Vol. 8, No. 3, May/June 1981, pages 353–357; and in "Generalised image combinations in dual k Vp digital radiography", L. A. Lehmann et al., MED. PHYS., Vol. 8, No. 5, Sept–Oct 1981, pages 659–667. These principles rely on the following basic assumption: in the case of all existing bodies, the space of the x-ray attenuation coefficients, considered as a function of the energy, is a two-dimensional space.

This assumption is physically justified by the fact that, at the energies of interest in the medical field, the absorption of x-rays results from only two phenomena. A first phenomenon is the Compton effect, a second phenomenon is the photoelectric effect. More precisely, the behavior of a given material M with respect to x-rays is entirely characterized by two scalar quantities. A first scalar quantity is the photoelectric absorption coefficient, denoted $a_p$, and the second scalar quantity is the Compton absorption coefficient, denoted $a_c$. The basic assumption is that there accordingly exist two functions of the energy $f_p(E)$ and $f_c(E)$ which are independent of the materials considered. These two functions are such that, irrespective of the material M and irrespective of the energy E, a mass attenuation coefficient $\mu_M(E)$ of any value may be written in the form:

$$\mu_M(E)\delta_M = a_p(M)19\, f_p(E) + a_c(M)\cdot f_c(E) \qquad \text{I}$$

where $a_p(M)$ and $a_c(M)$ are a function of the atomic number Z and of the mass number A of the material M considered; $\delta_M$ is the density of the material M. This amounts to saying that the functions $f_p(E)$ and $f_c(E)$ form a base of the space of the attenuation coefficients.

In practice, it is preferred to work in another base, the base vectors of which are two other functions of the energy E which are linearly independent. These base functions are the coefficients of attenuation of two different materials: for example on the one hand aluminum Al and on the other hand a polymethacrylate Po. In one of these materials, the photoelectric absorption is predominant whereas the Compton absorption is predominant in the other. Aluminum and polymethacrylate are chosen because aluminum has absorption properties close to that of bone and because polymethacrylate has absorption properties close to that of the soft tissues which surround the bones. This offers the advantage of reducing the errors which arise from a certain number of approximations involved in the method. It is clearly possible to choose another pair of materials at the outset. In particular, polymethacrylate could advantageously be replaced by water. Polymethacrylate has been chosen for its greater simplicity of use in a calibration stage which will be explained hereinafter. For the sake of easier understanding, a choice (Po, Al) will appear throughout the following description. However, theoretical reasoning is not absolutely dependent on this choice and other materials may accordingly be adopted for applications other than medical applications.

The change of base mentioned above is readily obtained by writing the relation I for the materials Al and Po:

$$\mu_{Al}(E)/\delta_{Al} = a_p(Al)\cdot f_p(E) + a_c(Al)\cdot f_c(E) \qquad \text{II}$$
$$\mu_{Po}(E)/\delta_{Po} = a_p(Po)\cdot f_p(E) + a_c(Po)\cdot f_c(E)$$

then by inverting the linear system II in order to obtain the expression of $f_p(E)$ and $f_c(E)$ as a function of $\mu_{Al}/\delta_{Al}$ and of $\mu_{Po}/\delta_{Po}$ and finally by replacing $f_p(E)$ and $f_c(E)$ by their expressions in the Equation I which is written for a material M.

The expression of the functions $f_p(E)$ and $f_c(E)$ can therefore be deduced from these two expressions II. These functions are now in turn given as a function of the global coefficients of absorption $\mu$ of aluminum and of polymethacrylate. If these functions $f_p(E)$ and $f_c(E)$ are then replaced in the first expression of $\mu_M(E)$ by their expressions as a function of $\mu_{Al}$ and $\mu_{Po}$, there is obtained an expression of the following form:

$$\mu_M(E)/\delta_M = K(M)\cdot\mu_{Al}(E)/\delta_{Al} + H(M)\cdot\mu_{Po}(E)/\delta_{Po} \qquad \text{III}$$

or else:

$$\mu_M(E) = K(M)\cdot\mu_{Al}(E)\cdot\delta_M/\delta_{Al} + H(M)\cdot\mu_{Po}(E)\cdot\delta_M/\delta_{Po} \qquad \text{IV}$$

where K(M) and H(M) are scalar quantities which depend on the numbers Z and A of the material M and of the materials Al and Po.

There is also employed a "plane of materials" defined as follows. Let us consider an x-ray which passes through an object composed, for instance, of a number of materials. At each point (x, y, z) of the object located on the path of the x-ray referred-to as the path C, we define the function $\mu(x,y,z,E)$ which is the value of the coefficient of attenuation of the material which is present in the object at the point (x,y,z) in respect of the energy E. Locally, each material has a coefficient of attenuation which verifies relation IV, that is to say which is expressed as a linear combination of $\mu_{Al}$ and $\mu_{Po}$. In consequence, the integral of the coefficients of attenuation along the path C verifies the following relation, irrespective of the energy E:

$$\int_C \mu(x,y,z,E)ds = t_{Po} \cdot \mu_{Po}(E) + t_{Al} \cdot \mu_{Al}(E) \qquad \text{V}$$

with $$t_{Po} = (1/\delta_{Po}) \cdot \int_C H(x,y,z)\delta_M(x,y,z)ds$$

and $$t_{Al} = (1/\delta_{Al}) \cdot \int_C K(x,y,z)\delta_M(x,y,z)ds$$

In these expressions, $t_{Al}$ and $t_{Po}$ are expressed in a unit of length and are referred-to as equivalent thicknesses of aluminum and polymethacrylate.

There is then defined an affine two-dimensional space designated as a "plane of materials" having a reference frame of orthonormal coordinates (O,i,j). An object traversed by an x-ray of any energy has in this affine space one and only one associated point M of coordinates ($t_{Po}$, $t_{Al}$). An object of polymethacrylate has an associated point carried by the axis Po which is collinear with i, an object of aluminum has an associated point carried by the axis Al which is collinear with j.

It will be seen that the polar coordinates ($t_m, \theta_M$) of a vector OM are particularly well suited to the representation of a homogeneous material. From expression V, there can be deduced in respect of a homogeneous material having a length L and irrespective of the energy E:

$$\mu_M(E)\cdot L = t_{Po}\cdot\mu_{Po}(E) + t_{Al}\cdot\mu_{Al}(E) \qquad \text{VI}$$

with $t_{Po} = H(M)\cdot\delta_M\cdot L/\delta_{Po}$ and $t_{Al} = K(M)\cdot\delta_M\cdot L/\delta_{Al}$ Two consequences are deduced from this formulation, in the plane of materials:

on the one hand, a given material is characterized by a ratio for this material between $t_{Al}$ and $t_{Po}$. This ratio is invariant by a change in thickness or even a change in density of the material. This means that the angle $\theta_M$ related to the axis Po of the half-line OM which bears the point M is characteristic of the material. In the case of bone, we shall thus refer to the characteristic angle of bone, namely $\theta_{os}$. We have the relation:

$$tg(\theta_M) = t_{Al}/t_{Po} = \{K(M)/H(M)\} \cdot \{\delta_{Al}/\delta_{Po}\} \qquad \text{VI bis}$$

furthermore, the norm of the vector OM which will be called the equivalent thickness $t_M$ is proportional to the product of density and thickness $\delta_M \cdot L$ of the material M:

$$t_M = |OM| = t_{Po}\cdot\cos\theta_M - t_{Al}\cdot\sin\theta_M \qquad \text{VI ter}$$
$$= \{H(M)\cdot\cos\theta_M/\delta_{Po} - K(M)\cdot\sin\theta_M/\delta_{Al}\}\cdot\delta_M\cdot L$$

If the density of the material M is not constant but spatially variable (this is the case of bone which may be more or less compact), then the equivalent thickness is proportional in this case to the integral, along the path C, of the density of the material considered. In accordance with the expression of $t_{Po}$ and $t_{Al}$ in V, we accordingly have:

$$t_{Po} = \int_C H(M)/\delta_{Po} \cdot \delta(x,y,z)ds \qquad \text{VII}$$

and $$t_{Al} = \int_C K(M)/\delta_{Al} \cdot \delta(x,y,z)ds$$

The angle $\theta_M$ is again defined by the ratio $t_{Al}/t_{Po}$ which is independent of the density:

$$tg(\theta_M) = t_{Al}/t_{Po} = \{K(M)/H(M)\} \cdot \{\delta_{Al}/\delta_{Po}\} \qquad \text{VII bis}$$

and the equivalent thickness, namely $|OM|$ has the value:

$$t_M = |OM| = \qquad \text{VII ter}$$
$$\{H(M)\cdot\cos\theta_M/\delta_{Po} + K(M)\cdot\sin\theta_M/\delta_{Al}\}\int_C \delta(x,y,z)ds$$

In the case which concerns the field of medicine, the object traversed by the x-ray is composed of several materials, at least bones and soft tissues having characteristic angles $\theta_{os}$ and $\theta_{ti}$ respectively.

It is agreed to consider here that all soft tissues are equivalent. This is not true insofar as, for example, muscles and fat do not have the same properties of absorption or in other words do not have the same coefficients $a_p$ and $a_c$. However, taking into account the fact that their angles are substantially comparable and in all cases far removed from that of bone, this approximation is justified.

In the plane of materials, the vector OM corresponding to the body can be represented as being the sum of the two vectors $OM_{os}$ and $OM_{ti}$ each corresponding to the contributions of bone and soft tissues. Each of these two vectors makes an angle of $\theta_{os}$ and $\theta_{ti}$ respectively with (O,i) and has a length of $t_{os}$ and $t_{ti}$ respectively. These lengths are proportional to the product of thickness and density of bone and soft tissue through which x-rays pass.

A knowledge of $\theta_{os}$ and $\theta_{ti}$ permits a change of reference frame in the plane of materials so as to change from the reference frame (O,i,j) to the reference frame (O,u,v), u being the unit vector carried by the axis of the soft tissues and v being the unit vector carried by the axis of the bones. Thus, the "bone and soft tissue equivalent lengths" may be expressed as a function of the "aluminum and polymethacrylate equivalent lengths":

$$t_{os} = \{-t_{Po}\sin\theta_{ti} + t_{Al}\cos\theta_{ti}\}/\sin(\theta_{os}-\theta_{ti}) \qquad \text{VIII}$$

$$t_{ti} = \{t_{Po}\sin\theta_{os} - t_{Al}\cos\theta_{os}\}/\sin(\theta_{os}-\theta_{ti})$$

It will now be seen that, for a given body, it is possible to determine the "equivalent thicknesses" $t_{Po}$ and $t_{Al}$ from radiation attenuation measurements carried out at two different x-radiation emission energies, said body being subjected to said radiations.

In the case of a monochromatic radiation having an energy E, the following relation may be written:

$$I = I_0 \cdot e^{-\int \mu M(x,y,z,E) \cdot ds} \qquad \text{IX}$$

where I is the radiation intensity measured on a detector after passing through the object and $I_0$ is the intensity which would be measured on the same detector if the radiation had not passed through the object ($I_0$ is designated hereinafter as the naked-light intensity).

Equation IX is readily converted to $$Ln(I_0/I) = -\int_C \mu_M(x,y,z,E) \cdot ds \qquad \text{IX bis}$$

By applying relation V, there is then obtained:

$$Ln(I_0/I) = t_{Po} \cdot \mu_{Po}(E) + t_{Al} \mu \text{hd Al}(E) \qquad \text{X}$$

It is postulated hereinafter that U or $V = Ln(I_0/I)$ according as the radiation energy employed is either of the two energies E1 and E2. Equation X written for each of the two energies makes it possible to obtain the system:

$$U = t_{Po} \cdot \mu_{Po}(E_1) + t_{Al} \mu_{Al}(E_1) \qquad \text{XI}$$

$$V = t_{Po} \cdot \mu_{Po}(E_2) + t_{Al} \mu_{Al}(E_2)$$

This system is readily reversed so as to obtain $t_{Po}$ and $t_{Al}$ as a function of the measurements $U_1$ and $U_2$:

$$t_{Po} = c_{11} \cdot U + c_{12} \cdot V \qquad \text{XII}$$

$$t_{Al} = c_{21} \cdot U + c_{22} \cdot V$$

The coefficients $c_{11}$, $c_{12}$, $c_{21}$, $c_{22}$ depend only on the coefficients of absorption of aluminum and of polymethacrylate at the energies $E_1$ and $E_2$.

In the real case encountered at the time of x-ray examination, the x-ray emission spectrum is not monochromatic. For example, when the x-ray tube is supplied with high voltage at 50 kV, the energies $E_1$ of the emitted x-rays are distributed between approximately 10 and 50 KeV. When the x-ray tube is supplied at 100 kV, the energies $E_2$ of the x-rays are distributed between 40 and 100 KeV.

The absorption of x-radiation having an energy spectrum S(E) through a body is accordingly expressed by the following equation XIII, a special case of which is given in Equation IX.

$$I = I_0 \cdot \int_E S(E) \cdot e^{\int_C -\mu M(x,y,z,E) \cdot ds} dE \qquad \text{XIII}$$

The situation here does not correspond to relation IX bis since, in this case, there is no longer any equality between the measurement $U(U = Ln(I_0/I))$ and the integral of the attenuation coefficients along the path C.

Should it be desired to apply the method of decomposition by dual energy explained earlier, it is consequently necessary to carry out a certain number of adaptations, both of physics to the method and of the method to physics.

The first adaptation consists in physically reducing the non-monochromatic appearance of the spectrum as far as possible. In order to modify the x-ray spectrum with a view to making it more similar to a monochromatic spectrum, the usual practice consists in carrying out a filtration of the radiation through a thickness of material (metallic material, for example) which absorbs the low energies (soft x-rays) to a greater extent than the high energies. In each spectrum, the contribution of the left portion of the spectrum will therefore be reduced. This has a further advantage in that the region of intersection of the two spectra corresponding to the two supply voltages of the x-ray tube is reduced and even made practically void. Thus, none of the energies of the spectrum $E_1$ is equal to an energy of the spectrum $E_2$.

Adaptation of the method to the spectral nature of the radiation involves generalization of the linear Equations XII in two Taylor developments of order p (to simplify, one adopts p=3) so as to take into account the inequality shown as a result of XIII. This generalization becomes:

$$t_{Po} = \qquad \text{XIV}$$

$$c_{11} + c_{12}U + c_{13}V + c_{14}U^2 + c_{15}V^2 + c_{16}UV + c_{17}U^3 + c_{18}V^3$$

$$t_{Al} =$$

$$c_{21} + c_{22}U + c_{23}V + c_{24}U^2 + c_{25}V^2 + c_{26}UV + c_{27}U^3 + c_{28}V^3$$

In this system, U designates the measurement performed in the case of radiation having an energy spectrum S1(E) or so-called "low-energy" radiation and V designates the measurement performed in the case of radiation having an energy spectrum S2(E) or so-called "high-energy" radiation. In this instance also, the coefficients $c_{ij}$ depend only on the characteristics of the base materials Al and Po.

The coefficients $c_{ij}$ are preferably estimated rather than determined theoretically during a calibration stage explained hereinafter.

The x-ray apparatus comprises a two-dimensional detector. The detector of this apparatus is subjected to a "low-energy" x-radiation when there is no object between the source and the detector, thus permitting measurement of the naked-light intensity $I_{01}$. The naked-light intensity $I_{02}$ is measured in the same manner for "high-energy" x-radiation.

A known thickness of aluminum $t_{Al}$ superposed on a known thickness of polymethacrylate $t_{Po}$ is then subjected to the same "low-energy" radiation, thus permitting measurement of the intensity $I_1$, then to the same "high-energy" radiation, which permits measurement of the intensity $I_2$. U and V are deduced therefrom.

The operation which consists in measuring $I_1$ and $I_2$ is renewed for a certain number of pairs ($t_{Po}$, $t_{Al}$), namely N pairs of stacked thicknesses of these materials. A point M in the "plane of materials" corresponds to each pair. Two corresponding pairs of points M1 and M2 such that the vectors OM1 and OM2 are not collinear are accordingly designated as "different pairs".

The Equations XIV are applied in the case of each pair. There are then obtained two systems of N linear equations written in a matrix form XV in which the unknowns are the coefficients $c_{ij}$, the matrix of the system being known as the "matrix of measurements":

$$\begin{vmatrix} t_{Po1} \\ t_{Po2} \\ \cdots \\ t_{PoN} \end{vmatrix} = \begin{vmatrix} 1 & U_1 & V_1 & U_1^2 & V_1^2 & U_1V_1 & U_1^3 & V_1^3 \\ 1 & U_2 & V_2 & U_2^2 & V_2^2 & U_2V_2 & U_2^3 & V_2^3 \\ \cdots & \cdots & \cdots & \cdots & \cdots & \cdots & \cdots & \cdots \\ 1 & U_N & V_N & U_N^2 & V_N^2 & U_NV_N & U_N^3 & V_N^3 \end{vmatrix} \begin{vmatrix} c_{11} \\ c_{12} \\ \cdots \\ c_{1N} \end{vmatrix} \quad \text{XV}$$

similarly in the case of aluminum:

$$\begin{vmatrix} t_{A11} \\ t_{A12} \\ \cdots \\ t_{A1N} \end{vmatrix} = \begin{vmatrix} \text{MATRIX OF MEASUREMENTS} \end{vmatrix} \begin{vmatrix} c_{21} \\ c_{22} \\ \cdots \\ c_{2N} \end{vmatrix}$$

In the case of a Taylor development of order 3, eight different pairs (N=8) are sufficient for inversion of the matrix of measurements and for calculation of the coefficients $c_{ij}$. In practice, it is found preferable to use much more than eight different pairs in the calibration stage, in which case the matrix of measurements is inverted in the least squares sense.

After the stage which has made it possible to determine the coefficients $c_{ij}$, the "low-energy" and "high-energy" acquisitions are made for the patient's body to be examined. Two measurements U and V per image element or pixel are then obtained for the acquired images. The equivalent thicknesses of polymethacrylate and aluminum are then the result of Equations XIV applied to these values U and V. The equivalent thicknesses of bones and soft tissues are then the result of Equations VIII.

In the case of conventional radiology (2D projection of the object on the 2D detector), the measurements of the intensities I and $I_0$ are replaced by the grey levels allotted to the pixels in the 2D image corresponding to the cells of the plane multidetector which intercept the path of the x-ray. Thus, if G is the grey level for a given pixel in the image with object and if $G_0$ is the grey level for the same pixel in the naked-light image, one writes: XVI $U = Ln(I_0/I) = Ln(G_0/G)$, and the same applies to V.

The equivalent thicknesses for the object to be examined must then be calculated pixel by pixel, starting from the measurements performed pixel by pixel in the "low-energy" and "high-energy" images. The result image or so-called "equivalent thickness image" is formed by assignment to each of its pixels of a grey level which is equal or proportional to the value of the equivalent thickness which is chosen or in other words calculated for said pixel.

There is then obtained, for example, a "bone equivalent thickness" in which the grey level is not zero, theoretically, solely in the case of the pixels corresponding to a ray which has passed through the bone. In the case of the pixels corresponding to the projection of a bone structure, the grey level is proportional to the product of bone density and thickness or more precisely to the integral of the bone density along the ray since the coefficient of proportionality does not depend on the materials (soft tissues) which are present around the bone.

In the calculation of the "equivalent thickness" image described earlier, it is implicitly assumed that the acquisition system employed is a "perfect" system which does not introduce any non-uniformities. Since this is not the case in actual fact, non-uniformities in measurements which are not corrected (or imperfectly corrected) accordingly result in errors in estimation of the equivalent thicknesses.

In the present state of the art, at the time of a "dual energy" combination, the coefficients $c_{ij}$ are estimated globally. These coefficients are estimated from measurements performed on two images (one for each energy) of a "stair-step" of polymethacrylate crossed with another "stair-step" of aluminum. Calibration measurements are then carried out for the thickness pairs which result from crossing of these "stair-steps".

In the present state of the art, it is possible to compensate for non-uniformities of the system by correcting the calibration measurements before calculating the coefficients $c_{ij}$, then by correcting the measurements relating to the patient's body prior to the polynomial combination. Such preliminary corrections require exact knowledge of the transfer function of the system in respect of each point of the two-dimensional image, which is made difficult by the dependence on numerous parameters (energies, intensities, geometry, defects of the detector, and so on). Moreover, even if this transfer function were well known, the application of these corrections would be laborious since they would have to be made on all the measurements.

In the case of selective 3D reconstruction from images combined by dual energy, it is necessary to ensure that the "equivalent thickness" images carry quantitative information. For example, in the case of a "bone equivalent thickness" image, the grey level of each pixel must in fact be proportional to the real thickness of bone through which the radiation passes or else to the integral of the bone densities along the path (the coefficient of proportionality being spatially constant). If this condition is not satisfied, the data used for the reconstruction will be known as "non-consistent" and will give rise to the generation of reconstruction artifacts.

The aim of the invention is to overcome these disadvantages without otherwise imposing uniformity compensations in the production of all the images: acquired images, images of materials and images produced by dual-energy combination. In order to obtain quantitative information over the entire image, it is preferred not to make an a priori correction of the system but rather to consider at the outset that each cell of the detector is an independent detector and the equivalent thickness is estimated cell by cell, thus implying that a set of coefficients $c_{ij}(x,y)$ corresponds to each cell (x,y) of the detector and depends on the position of said cell. The generalization adopted in XIV makes it possible to take into account in the case of each cell measurement distortions which have been described earlier and result in particular in inaccuracy of the Formula XVI. In this manner, the non-uniformity correction is integrated in the calculation of equivalent thicknesses at the moment of calculation of energy combination. In consequence, no compensation correction has to be performed. The uniformity compensation is carried out pixel by pixel when calculating the equivalent thicknesses with coefficients which already provide for compensation.

SUMMARY OF THE INVENTION

The invention is therefore directed to a method for calibrating the measuring system of an x-ray apparatus intended for an acquisition involving two stages, each stage being conducted with a different x-radiation energy, in which one of said two-energy x-radiations is emitted during these two stages with an x-ray tube of said apparatus towards the body of a patient to be examined, at least one projected image of the body is acquired during each of these two stages, these images being constituted by collections of results of measurement, at the location of cells of a multi-cell detector of said apparatus, of the absorption of said x-radiations in said body, these results of measurement of x-ray absorption of each stage aforesaid are processed by effecting a dual-energy combination of said acquired projected images whilst the x-radiation is emitted with different energies, said processing operation involves a calibration, said calibration involves beforehand in the case of these two energies specific measurements of absorption of said x-radiations through stacks of two materials which cover the entire surface area of the detector, these two materials have different x-ray adsorption behaviors, said specific measurements are intended to obtain two groups of coefficients which describe respectively the x-ray absorption behavior of each of said two materials as a function of the value of the energy, said method being distinguished by the fact that said calibration is performed detector cell by detector cell in order to obtain two groups of coefficients for each cell of the detector.

In a practical application, the detector is a two-dimensional detector of the brightness amplifier type.

Seeing that the calculation of the sets of coefficients $c_{ij}(x,y)$ for each cell is a laborious undertaking since it leads to inversion of a measurement matrix (in addition in the least squares sense) as many times as there are cells in the detector, an improvement of the present invention consists in avoiding the need to estimate the coefficients $c_{ij}(x,y)$ in every cell of the detector. However, in order to take into account their spatial variation, which is a low-frequency variation, one estimates the coefficients in a certain number of cells which are disposed on a square lattice of the detector such as $32 \times 32$ cells, for example. One then estimates the coefficients for the intermediate cells by a method of interpolation such as a method of bilinear interpolation, for example

BRIEF DESCRIPTION OF THE DRAWINGS

FIG. 1 is a schematic representation of an x-ray apparatus in which the method according to the invention can be employed.

FIG. 2 is a schematic representation of the mode of energy combination for the purpose of producing another image.

FIG. 3 is a schematic representation of the non-monochromatic character of the real x-radiations.

FIG. 4 shows the effects of non-uniformity of the detection efficiency of the x-ray detectors.

FIG. 5 shows one of the stages of the method in accordance with the invention.

DETAILED DESCRIPTION OF THE INVENTION

FIG. 1 illustrates an apparatus in which the method in accordance with the invention can be employed. In this apparatus, a 2D x-ray acquisition system essentially comprising an x-ray tube 1 provided with its electronic control circuits (not specifically illustrated) irradiates the body 2 of a patient who is placed on a support bed 3. On the side remote from the x-ray tube 1 with respect to the bed 3 is placed a so-called 2D detector 4 which receives the x-radiation after said radiation has passed through the body 2. In one example, the detector 4 can comprise an x-ray image intensifier coupled to a camera. The signal delivered by the detector 4 is directed to a processing device 5 which essentially comprises an arithmetic and logic unit and memories. The processing device 5 can perform digitization of the acquired images and processing of these latter in accordance with the invention. These images are then stored in a memory 6. A display monitor 7 as well as an associated display software package serve to represent the bone structures as if the surrounding tissues had been dissected.

FIG. 2 illustrates a bone acquisition protocol and shows that a projected image 14 obtained whilst the x-ray tube emits radiation with a given spectrum can be combined with another projection 18 obtained whilst the x-ray tube emits a different energy spectrum. By combining the pixel data of the projected images 14 and 18 in pairs in accordance with an energy combination mode mentioned above, it is possible to produce another projected image 19 which is representative of the bone structure alone.

FIG. 3 shows that the x-ray emission spectrum is not monochromatic. For example, when the x-ray tube is supplied with high voltage at 50 kv, the energies $E_1$ of the emitted x-rays are distributed between approximately 10 and 50 keV. When the x-ray tube is supplied at 100 kv, the x-ray energies $E_2$ are distributed between 40 and 100 kEV. The x-ray spectrum is shown in FIG. 3 in respect of supply voltages of 50 and 100 kV.

Different defects brought about by the system of acquisition of two-dimensional x-ray images have made it necessary in the present invention to adapt the calibration stage so as to include a correction of these defects. In the first place as shown in FIG. 4, the efficiency of the detector cells is not uniform over the entire surface of the detector and is not a linear function of the incident intensity. For example, this efficiency is more attenuated on the edges of the detection field of the detector. At the center of the field, said efficiency is also attenuated but to a lesser extent. In the second place, the x-ray emission spectrum is not isotropic. Finally, the scattered radiation introduces a supplementary difference between the measurements U and V, and the integral of the adsorption coefficients.

Thus, when the detector is exposed to radiation through homogeneous material of constant thickness or else when a "naked-light" picture is taken, the grey level obtained in the picture is not uniform but exhibits "low-frequency" variations, one example of which is given in FIG. 4. This example is obtained with a detector of the x-ray image intensifier type which is coupled to a camera. The thickness of the deposit of intensifier material in this detector as well as other factors make said variation continuous and of low frequency. Moreover, "densitometric distortions" depend on a large number of factors such as the geometrical parameters of the acquisition (distance from source to detector, distance from object to detector, radius of curvature of the detector, and so on), the exact nature of the x-ray emission spectrum in all directions (since the spectrum is not isotropic), the efficiency of the image amplifier as a function of the energy and the intensity of the incident rays, and so on.

The calculation of the sets of coefficients $c_{ij}(x,y)$ for each cell of the detector is a laborious process since it leads to inversion of a measurement matrix (in addition in the least squares sense) as many times as there are cells in the detector. In order to avoid the need to estimate the coefficients $c_{ij}(x,y)$ at each point of the detector while at the same time taking their spatial variation into account in the case of detectors which exhibit a continuous low-frequency variation as described earlier, it has been chosen in this method to estimate the coefficients in a certain number of cells such as the cell 8 (FIG. 1) disposed on a square lattice of the detector such as 32×32, for example. The coefficients are then estimated for the intermediate cells by means of a method of interpolation such as a bilinear interpolation, for example.

The measurements for each of the 32×32 cells are carried out from a set of images or so-called calibration charts which are the images obtained by interposing between the source and the detector a plate 23 of constant thickness $t_{Po}$ of polymethacrylate superposed on a plate 24 of constant thickness $t_{Al}$ of aluminum, in respect of a certain number of pairs of thicknesses ($t_{Po}$, $t_{Al}$). The area of the plates is larger than the useful area of the detector in order to prevent edge effects. This set of charts contains all the data which are necessary for calibration.

Calculation of the measurements $Ln(G_0/G)$ for each of the 32×32 cells chosen is preferably carried out by replacing $G$ and $G_0$ by a value estimated on a window which is centered around the point chosen. By way of example, this value is the mean value of the grey levels on the window, or else the median value, with a view to limiting the errors introduced by quantum noise.

What is claimed is:

1. A method for calibrating the measuring system of an x-ray apparatus intended for an acquisition involving two stages, each stage being conducted with a different x-ray energy, in which two-energy x-radiations are emitted during said two stages with an x-ray tube of said apparatus towards the body of a patient to be examined, at least one projected image of the body is acquired during each of these two stages, these acquired images being constituted by collections of results of measurement, at the location of cells of a multi-cell detector of said apparatus, of the absorption of said x-radiations in said body, these results of measurement of x-ray absorption of each stage aforesaid are processed by effecting a dual-energy combination of the image elements of said acquired projected images, said processing operation involves a calibration, said calibration involves beforehand in the case of these two energies specific measurements of x-ray absorption through stacks of two materials which cover the entire surface area of the detector, these two materials have different x-ray absorption behaviors, said specific measurement are used to obtain two groups of coefficients which describe respectively the x-ray absorption behavior of each of said two materials as a function of the value of the energy, said calibration is performed detector cell by detector cell in order to obtain two groups of coefficients for each cell of the detector wherein, in order to carry out the calibration cell by cell, one measures the effect of absorption at the location of the cells of a set of selected cells, one calculates the coefficients of the groups of coefficients in said selected cells, one deduces by bilinear interpolation the coefficients in intermediate cells between said selected cells.

2. A method according to claim 1, wherein the detector is a two-dimensional detector which provides for its cells continuous low-frequency variations of its detection characteristics.

3. A method according to claim 1, wherein the energy combination involves the formation of at least one other image in which the value assigned to each pixel is a function of an equivalent thickness of one of said two materials.

4. A method for calibrating the measuring system of an x-ray apparatus intended for an acquisition involving two stages, each stage being conducted with a different x-ray energy, in which two-energy x-radiations are emitted during said two stages with an x-ray tube of said apparatus towards the body of a patient to be examined, at least one projected image of the body is acquired during each of these two stages, these acquired images being constituted by collections of results of measurement, at the location of cells of a multi-cell detector of said apparatus, of the absorption of said x-radiations in said body, these results of measurement of x-ray absorption of each stage aforesaid are processed by effecting a dual-energy combination of the image elements of said acquired projected images, said processing operation involves a calibration, said calibration involves beforehand in the case of these two energies specific measurements of x-ray absorption through stacks of two materials which cover the entire surface area of the detector, these two materials have different x-ray absorption behaviors, said specific measurement are used to obtain two groups of coefficients which describe respectively the x-ray absorption behavior of each of said two materials as a function of the value of the energy, said calibration is performed detector cell by detector cell in order to obtain two groups of coefficients for each cell of the detector wherein, in order to carry out the calibration cell by cell, one measures the effect of absorption at the location of the cells of a set of selected cells, one calculates the coefficients of the groups of coefficients in said selected cells, one deduces by bilinear interpolation the coefficients in intermediate cells between said selected cells wherein, in order to measure the effects of absorption at the location of a set of selected cells, one determines windows centered on each of said selected cells, and one performs a statistical calculation on the measurements of x-ray detection in cells adjacent to the selected cell and contained in the window.

* * * * *